United States Patent [19]
Harandi et al.

[11] Patent Number: 4,975,097
[45] Date of Patent: Dec. 4, 1990

[54] ISO-OLEFIN ETHERIFICATION, UPGRADING AND PARAFFIN TRANSHYDROGENATION

[75] Inventors: Mohsen N. Harandi, Lawrenceville; Hartley Owen, Belle Mead, both of N.J.

[73] Assignee: Mobil Oil Corporation, New York, N.Y.

[21] Appl. No.: 454,473

[22] Filed: Dec. 21, 1989

Related U.S. Application Data

[63] Continuation-in-part of Ser. No. 179,729, Apr. 11, 1988, abandoned, which is a continuation-in-part of Ser. No. 130,261, Dec. 8, 1989, Pat. No. 4,826,507.

[51] Int. Cl.⁵ .......................... C10L 1/18; C07C 41/06
[52] U.S. Cl. .......................................... 44/77; 568/697
[58] Field of Search ...................... 44/77, 53; 585/310

[56] References Cited
U.S. PATENT DOCUMENTS

| | | | |
|---|---|---|---|
| 4,191,846 | 3/1980 | Farah et al. | 585/440 |
| 4,193,770 | 3/1980 | Chase et al. | 44/56 |
| 4,252,541 | 2/1981 | Herbstman | 44/56 |
| 4,329,516 | 5/1982 | Al-Muddarris | 568/697 |
| 4,377,393 | 3/1983 | Schleppinghoff | 44/63 |
| 4,413,150 | 11/1983 | Briggs | 568/697 |
| 4,546,204 | 10/1985 | Parris | 568/697 |
| 4,554,386 | 11/1985 | Groeneveld et al. | 568/697 |
| 4,806,695 | 2/1989 | Vora et al. | 568/697 |
| 4,826,507 | 5/1989 | Harandi et al. | 44/77 |
| 4,827,046 | 5/1989 | Harandi | 568/697 |
| 4,830,635 | 5/1989 | Harandi et al. | 44/56 |

Primary Examiner—Olik Chaudhuri
Assistant Examiner—E. McAvoy
Attorney, Agent, or Firm—Alexander J. McKillop; Charles J. Speciale; L. G. Wise

[57] ABSTRACT

A technique for converting olefinic light hydrocarbons to ether-rich liquid fuels and olefinic gasoline including etherification, olefin upgrading and transhydrogenation operations. The preferred process includes: reacting a fresh hydrocarbon stream containing $C_{4+}$ iso-alkene with lower aliphatic alcohol in an etherification zone in contact with an acidic etherification catalyst under etherification conditions whereby an effluent stream containing $C_{5+}$ tertiary-alkyl ether is produced; separating the etherification effluent stream to provide a first liquid stream comprising $C_{5+}$ ether and a second stream comprising unreacted alcohol and $C_{4+}$ hydrocarbons; contacting the second stream with acidic metallosilicate catalyst for conversion of oxygenates and olefins under olefin oligomerization and isomerization conditions at elevated temperature; separating oligomerization effluent to recover an intermediate hydrocarbon stream rich in $C_{4+}$ paraffinic hydrocarbon, a light gas stream, and a liquid product stream comprising $C_{6+}$ olefinic gasoline; contacting the $C_{4+}$ intermediate hydrocarbon stream with lower alkene in the presence of transhydrogenation catalyst whereby $C_{4+}$ paraffin is converted to $C_{4+}$ olefin, including iso-alkene; separating transhydrogenation effluent to recover $C_{4+}$ olefin containing iso-alkene; and passing at least a portion of iso-alkene to the etherification zone for co-conversion with fresh hydrocarbon and alcohol to produce tertiary-alkyl ether.

19 Claims, 2 Drawing Sheets

ISO-OLEFIN ETHERIFICATION, UPGRADING AND PARAFFIN TRANSHYDROGENATION

Reference to Copending Application - This application is a continuation-in-part of Ser. No. 07/179,729 filed 4/11/88, now abandoned, which is a continuation-in-part of Ser. No. 130,261, filed 12/08/87, now U.S. Pat. No. 4,826,507, incorporated by reference.

BACKGROUND OF THE INVENTION

This invention relates to processes for converting lower aliphatic alcohol, such as methanol, and olefinic hydrocarbons to high octane liquid fuel. In particular, this invention relates to a system for the production of tertiary-alkyl ethers in the presence of a lower alkanol, such as methanol, combined with the conversion of olefins to gasoline and a transhydrogenation step to convert branched paraffins to branched olefins for recycle.

Technical progress in catalytic olefins upgrading, oxygenate conversion to lower olefins (e.g.- methanol-to-olefins - "MTO"), and the commercial methanol-to-gasoline ("MTG") process have provided important synthetic fuel sources. Also, there has been considerable development of processes synthetic alkyl tertiary-alkyl ethers as octane boosters in place of conventional lead additives in gasoline. The etherification processes for the production of methyl tertiary alkyl ethers, in particular methyl t-butyl ether (MTBE) and t-amyl methyl ether (TAME) have been the focus of considerable research attention to resolve certain limitations in the etherification process with respect to the opportunity to drive the equilibrium dependent etherification reaction to completion by conducting etherification in the presence of excess methanol. It is known that recovering unreacted methanol by conventional separation and extraction techniques imposes severe economic burdens on the etherification process.

Recognizing the common feedstock (e.g. - methanol) for the synthetic production of gasoline as well as the production of methyl tertiary alkyl octane boosting ethers, research workers have endeavored to combine these processes in a manner to provide a synergistically beneficial integrated process.

It is known that isobutylene and other isoalkenes produced by hydrocarbon cracking may be reacted with methanol, ethanol, isopropanol and other lower aliphatic primary and secondary alcohols over an acidic catalyst to provide tertiary ethers. Methanollis considered the most important $C_1-C_4$ oxygenate feedstock because of its widespread availability and low cost. Therefore, primary emphasis herein is placed on MTBE and TAME.

In recent years, a major technical challenge presented to the petroleum refining industry has been the requirement to establish alternate processes for manufacturing high octane gasoline in view of the regulated requirement to eliminate lead additives as octane enhancers as well as the development of more efficient, higher compression ratio gasoline engines requiring higher octane fuel. To meet these requirements the industry has developed non-lead octane boosters and has reformulated high octane gasoline to incorporate an increased fraction of aromatics. While these and other approaches will fully meet the technical requirements of regulations requiring elimination of gasoline lead additives and allow the industry to meet the burgeoning market demand for high octane gasoline, the economic impact on the cost of gasoline is significant. Accordingly, workers in the field have intensified their effort to discover new processes to manufacture the gasoline products required by the market place. One important focus of that research is a new process to produce high octane gasolines blended with lower aliphatic alkyl ethers as octane boosters and supplementary fuels. $C_5-C_7$ methyl alkyl ethers, especially methyl t-butyl ether (MTBE) and t-amyl methyl ether (TAME) have been found particularly useful for enhancing gasoline octane. Therefore, improvements to the processes related to the production of these ethers are matters of high importance and substantial challenge to research workers in the petroleum refining arts. It is known that isobutylene may be reacted with methanol over an acidic catalyst to provide methyl tertiary butyl ether (MTBE) and iso-amylenes may be reacted with methanol over an acidic catalyst to produce t-amyl methyl ether (TAME). In these etherification processes, a problem of major importance is that methanol is not totally converted and the separation of methanol from the etherification reaction product due to the proclivity of methanol to form a very dilute azeotropic mixture with hydrocarbons and the strong solubility of methanol in both water and hydrocarbons. While it would be beneficial from an equilibrium standpoint to use large excesses of methanol in etherification, subsequent separation problems have limited that process improvement. Due largely to these factors, the cost associated with conventional methanol separation and recycling in the etherification reaction represents approximately 30% of the cost of the total etherification process.

In U.S. Pat. No. 4,684,757 to Avidan et al., the well-known ability of zeolite type catalyst to convert methanol to olefins is utilized by directing unreacted methanol from an etherification reaction to a zeolite catalyzed conversion reaction for conversion to olefin, thereby obviating the need to separate and recycle methanol in the etherification reaction. However, the process incorporates an alkylation step in one embodiment to produce alkylate as well as $C_5+$ gasoline and $C_5+$ ethers.

The process for the conversion of methanol to olefins utilized in the Avidan et al. patent is but one in a series of analogous processes based upon the catalytic capabilities of zeolites. It is known that medium pore acid zeolites, such as ZSM-5, can convert methanol to hydrocarbons of higher average molecular weight. Depending on various conditions of space velocity, temperature and pressure methanol, and lower oxygenates in general, can be converted in the presence of zeolite type catalyst to olefins which may then oligomerize to provide gasoline or distillate or may be converted further to produce aromatics.

The feasibility and adaptability of the basic chemistry of zeolite oxygenates conversion to produce useful conversion processes has been the subject of much inventive research activity. Recent developments in zeolite catalyst and hydrocarbon conversion processes have created interest in using oxygenates and olefinic feedstocks for producing $C_5+$ gasoline, diesel fuel, etc. In addition to the basic work derived from ZSM-5 type zeolite catalyst, a number of discoveries have contributed to the development of a new industrial process. This process has significance as a safe, environmentally acceptable technique for utilizing feedstocks that contain lower olefins, especially $C_2-C_5$ alkenes. In U.S. Pat. Nos. 3,960,978 and 4,021,502, Plank, Rosinski and Givens disclose conversion of $C_2$–$C_5$ olefins, alone or in admixture with paraffinic components into higher hydrocarbons over crystalline zeolites having controlled acidity. Reaction conditions of moderate severity favor the conversion of olefins to predominantly gasoline boiling range products with little paraffins conversion. Milder reaction temperatures and high operating pressures can produce distillate range fuels as well from lower olefins. Garwood et al. have also contributed improved processing techniques in U.S. Pat. Nos. 4,150,062, 4,211,640 and 4,227,992. The above identified disclosures are incorporated herein by reference.

A well-known process for the conversion of oxygenates to gasoline is the methanol to gasoline process, known as MTG. The process is described in U.S. Pat. No. 3,931,349 to Kuo, U.S. Pat. No. 4,404,414 to Penick et al. and in the publication by C. D. Chang, Catal. Rev.-Sci. Eng., 25, 1 (1983). These references are incorporated herein in their entirety.

Recognizing the limiting problems of the etherification processes to produce MTBE and TAME and the potential that resides in the general area of the chemistry of oxygenate and olefin conversion with zeolites to resolve those problems, the following objectives of the instant invention have been established: It is an object of the present invention to provide an improved process for the production of high octane gasoline incorporating lower alkyl tertiary-alkyl ethers from isoalkene-rich hydrocarbons, especially MTBE manufacture. It is another object of the present invention to provide an integrated process and reactor system for production of liquid fuels from isoalkene-rich hydrocarbons incorporating etherification with alkanol and olefins conversion and transfer dehydrogenation of paraffins, especially branched C4–C5 isoalkanes.

SUMMARY OF THE INVENTION

It has been discovered that high octane gasoline can be produced employing an improved etherification process that can utilize lower alcohols such as methanol.

In a preferred embodiment, a continuous process is provided for converting olefinic hydrocarbon and alcohol to alkyl tert-alkyl ethers and gasoline comprising the following steps: contacting lower alkanol feedstock with a C4+hydrocarbon feedstream rich in isobutene in a first etherification catalytic reaction zone for contact with acid etherification catalyst under etherification process conditions for converting alkanol and isobutene to predominantly alkyl tertiary-butyl ether; fractionating etherification effluent to recover overhead vapor containing unreacted alkanol and light olefinic hydrocarbon and to recover liquid product containing alkyl tertiary-butyl ether; catalytically converting said overhead vapor in contact with medium pore acid zeolite catalyst in a second catalytic reaction zone to provide predominantly liquid $C_5+$ hydrocarbon product along with $C_3$–$C_4$ aliphatic hydrocarbon intermediate product rich in isobutane, and a light gas byproduct; separating the light gas, $C_3$–$C_4$ isobutane-rich intermediate and $C_5+$ hydrocarbon product; transhydrogenating isobutane-rich intermediate by reaction with ethene or propene to produce isobutene; and recycling isobutene from transhydrogenation effluent for reaction with alkanol feedstock.

DETAILED DESCRIPTION OF THE INVENTION

Figure 1:
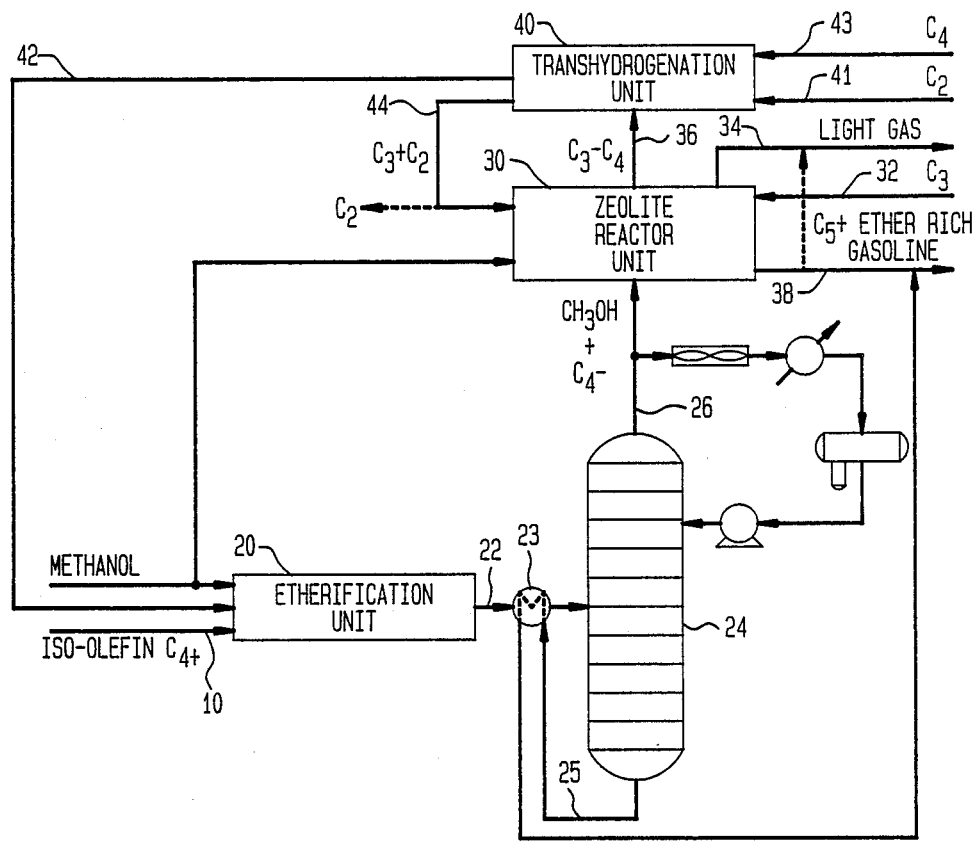
FIG. 1 is a schematic process flow sheet of the present invention.

The zeolite conversion processes for MTO, MTG and olefin upgrading (sometimes known as Mobil Olefin-to-Gasoline - "MOG") are closely related processes employing medium pore size shape selective zeolite type catalyst whose operating conditions may be optimized to shift the conversion reaction toward the production of olefins and the conversion of olefins to gasoline. These processes are further integrated in a novel way through a unique transhydrogenation step to yield the fully integrated process of the instant invention. These known processes are discussed further herein. However, in FIG. 1, the fully integrated process of the present invention incorporating these individual processes is presented in a schematic drawing.

Referring now to the drawing, a schematic diagram of a preferred embodiment of the present invention is presented. Etherification hydrocarbon feedstream 10 preferably comprises a $C_4+$ hydrocarbon stream rich in isoalkenes, such as a fluid catalyst cracking unit light gas containing isobutene. The hydrocarbon stream is passed to etherification reactor 20 and mixed with methanol. A unique advantage of the present invention is the capability to use large stoichiometric excesses of methanol in the etherification reaction, thereby promoting the improved formation of ethers. Excess methanol in the range of 2 to 50% may be conveniently used. The etherification reaction is conducted preferably at about 60° C. The etherification effluent is passed via line 22 and heat exchange 23 to a fractionator tower 24, wherein a bottom stream 25 is separated comprising ether-rich gasoline. The overhead stream 26 from the fractionator comprises etherification excess methanol and unreacted light hydrocarbon. The mixture is passed to a zeolite reactor 30 for conversion of aliphatic hydrocarbons and oxygenates, supplemented, optionally, by a stream 32 of $C_3-$ olefinic hydrocarbons, such as FCC light offgas. Olefins are converted predominantly to gasoline at a pressure between 420 kPa and 2100 kPa (60 and 300 psia) and a temperature of about 200° to 500° C. Under these conditions methanol in the mixture is also converted to higher hydrocarbons including $C_3$–$C_4$ isoparaffins. The zeolite conversion effluent is passed to a fractionation unit (not shown) for the separation of $C_2-$ light fuel gas 34, $C_3$–$C_4$ paraffins 36 and a $C_5$–$C_9$ gasoline product 38.

The $C_3$–$C_4$ paraffins, rich in isobutane, are passed to transhydrogenation zone 40 for reaction with a lighter olefinic gas stream 41 comprising ethene (or propene if the light gas has been removed from stream 26). Optional isobutane may be introduced to the transhydrogenation unit as supplemental feedstream 43. $C_4$ olefins are recovered from transhydrogenation effluent stream 42 and passed to the etherification zone 20. Optionally, a $C_3-$ olefin stream 44 may also be recovered and recycled for further olefins-to-gasoline conversion in the zeolite reactor zone 30.

Advantageously, C3 components leaving reactor 30 can be sent to unit 40 for conversion to propene which can be upgraded in the reactor unit 30. Also, the transhydrogenation reaction reactor effluent can be fed to the etherification unit without separating or efficiently separating C3− components from C4-components. This will allow utilizing unit 30 separation section as the only gas plant in the process.

Figure 2:
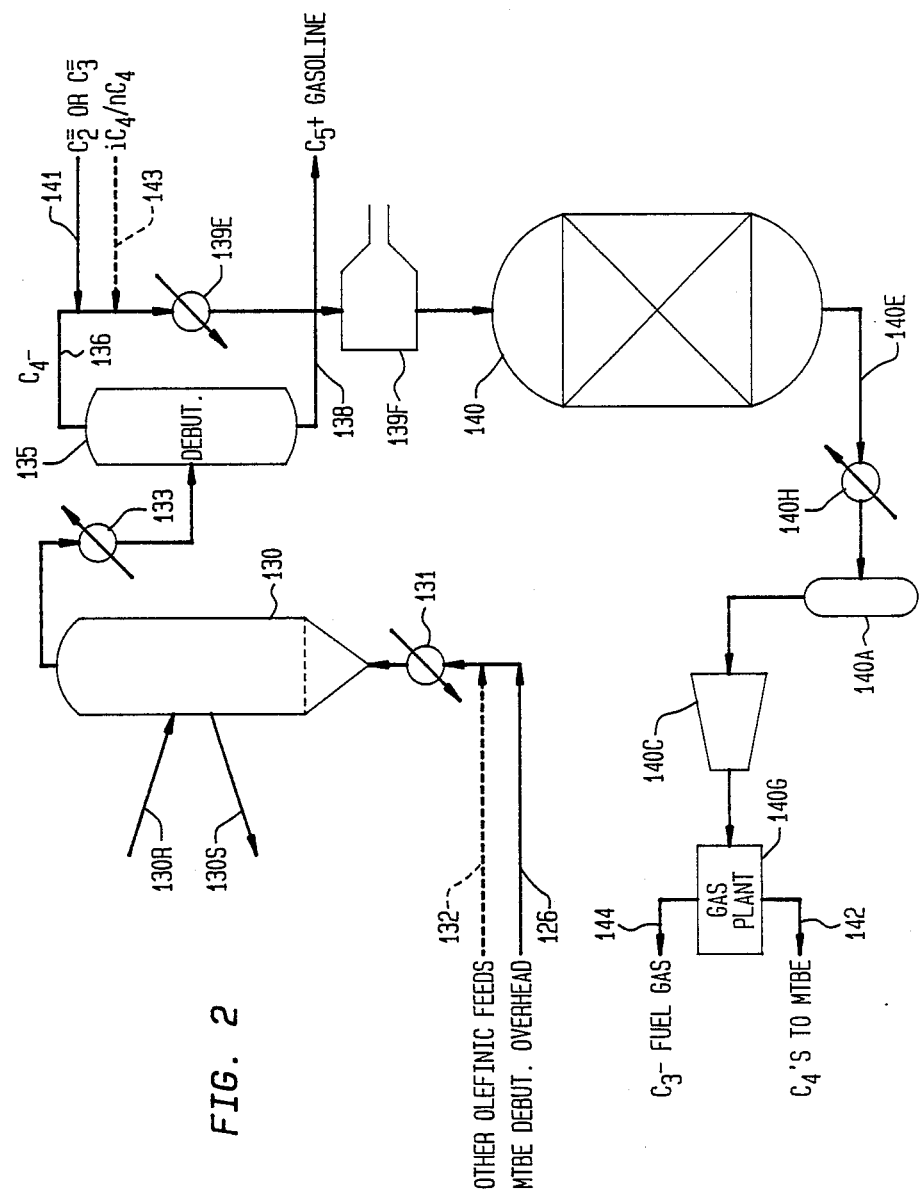
FIG. 2 is a detailed embodiment showing process and equipment configuration for an olefin upgrading and transhydrogenation system.

The embodiment depicted in FIG. 2 provides details of a preferred fluidized bed reactor 130 containing finely divided zeolite catalyst particles for upgrading unreacted olefins and methanol from the MTBE debutanizer overhead stream 126, with optional olefinic feed being added via line 132 and heating to reaction temperature in exchanger unit 131. Reactor means 130 is provided with catalyst handling means 130R for adding regenerated or fresh catalyst particles and spent catalyst withdrawal means 130S. Reactor effluent is cooled in exchanger unit 133 and fractionated in debutanizer unit 135 to provide a C5+ gasoline product stream 138 and an overhead stream 136 containing isobutane produced in the reactor system or carried through from the C4 feedstock. This stream can be premixed with lower olefin stream 141 containing ethene and/or propene for transhydrogenation, and optional isobutane or n-butane may be added to increase butenes production in the downstream reactor 140. After heating in exchanger 139E and furnace 139F, the mixture of reactants is contacted with transhydrogenation catalyst in fixed bed reactor 140. The reactor effluent stream 140E is cooled in exchanger 140H, passed through accumulator 140A, compressor 140C and processed in gas plant 140G to recover a recycle C4 stream 142 for etherification and a light gas stream 144 containing propane, unreacted propene, ethane, and unreacted ethene, which may be taken off the process loop for use as fuel gas or the like.

ETHERIFICATION OPERATION

The reaction of methanol with isobutylene and isoamylenes at moderate conditions with a resin catalyst is known technology, as provided by R. W. Reynolds, et al., *The Oil and Gas Journal*, June 16, 1975, and S. Pecci and T. Floris, *Hydrocarbon Processing*, Dec. 1977. An article entitled "MTBE and TAME - A Good Octane Boosting Combo", by J. D. Chase, et al., *The Oil and Gas Journal*, Apr. 9, 1979, pages 149–152, discusses the technology. A preferred catalyst is a sulfonic acid ion exchange resin which etherifies the reactants. such as Amberlyst 15 resin. Other acid catalysts such as Zeolite Beta or other zeolites may be employed.

Processes for producing and recovering MTBE and other methyl tert-alkyl ethers for $C_4$–$C_7$ iso-olefins are known to those skilled in the art, such as disclosed in U.S. Pat. Nos. 4,788,365 and 4,820,877 (Harandi et al). Various suitable extraction and distillation techniques are known for recovering ether and hydrocarbon streams from etherification effluent.

CONVERSION OF METHANOL AND HYDROCARBONS TO LIQUID HYDROCARBONS

Zeolite catalysis technology for upgrading lower aliphatic hydrocarbons and oxygenates to liquid hydrocarbon products are well known. Commercial Methanol-to-Gasoline (MTG), methanol-to olefins (MTO), aromatization (M2-Forming) and Mobil Olefin to Gasoline/Distillate (MOG/D) processes employ shape selective medium pore zeolite catalysts for these processes. It is understood that the present zeolite conversion unit operation can have the characteristics of these catalysts and processes to produce a variety of hydrocarbon products, especially liquid aliphatic and aromatics in the $C_5$–$C_9$ gasoline range.

Description of Zeolite Catalysts

Recent developments in zeolite technology have provided a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, Fe or mixtures thereof, within the zeolite framework. These medium pore zeolites are favored for acid catalysis; however, the advantages of ZSM-5 structures may be utilized by employing highly siliceous materials or crystalline metallosilicate having one or more tetrahedral species having varying degrees of acidity. ZSM-5 crystalline structure is readily recognized by its X-ray diffraction pattern, which is described in U.S. Pat. No. 3,702,866 (Argauer, et al.), incorporated by reference.

Zeolite hydrocarbon upgrading catalysts preferred for use herein include the medium pore (i.e., about 5–7A) shape-selective crystalline aluminosilicate zeolites having a silica-to-alumina ratio of at least 12, a constraint index of about 1 to 12 and acid cracking activity (alpha value) of about 1–250, preferably about 3 to 80 based on total catalyst weight. In the fluidized bed reactor the coked catalyst may have an apparent activity (alpha value) of about 3 to 80 under the process conditions to achieve the required degree of reaction severity. Representative of the ZSM-5 type medium pore shape selective zeolites are ZSM-5, ZSM-11, ZSM-12, ZSM-22, ZSM-23, ZSM-35, and ZSM-48. Aluminosilicate ZSM-5 is disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245; 4,414,423; 4,417,086; 4,517,396 and 4,542,251. The disclosures of these patents are incorporated herein by reference. While suitable zeolites having a coordinated metal oxide to silica molar ratio of 20:1 to 200:1 or higher may be used, it is advantageous to employ a standard ZSM-5 having a silica alumina molar ratio of about 25:1 to 70:1, suitably modified if desired to adjust acidity and oligomerization/aromatization characteristics. A typical zeolite catalyst component having Bronsted acid sites may consist essentially of aluminosilicate ZSM-5 zeolite with 5 to 95 wt. % silica and/or alumina binder.

Usually the zeolite crystals have a crystal size from about 0.01 to 2 microns or more. In order to obtain the desired particle size for fluidization in the turbulent regime, the zeolite catalyst crystals are bound with a suitable inorganic oxide, such as silica, alumina, etc. to provide a zeolite concentration of about 5 to 95 wt. %. It is advantageous to employ a standard ZSM-5 having a silica:alumina molar ratio of 25:1 or greater in a once-through fluidized bed unit to convert 60 to 100 percent, preferably at least 75 wt. %, of the mono-alkenes and methanol in a single pass. In the preferred embodiment 25% H-ZSM-5 catalyst calcined with 75% silica-alumina matrix binder is employed unless otherwise stated.

Particle size distribution can be a significant factor in achieving overall homogeneity in turbulent regime fluidization. It is desired to operate the process with particles that will mix well throughout the bed. Large particles having a particle size greater than 250 microns should be avoided, and it is advantageous to employ a particle size range consisting essentially of 1 to 150 microns. Average particle size is usually about 20 to 100 microns, preferably 40 to 80 microns. Particle distribution may be enhanced by having a mixture of larger and smaller particles within the operative range, and it is particularly desirable to have a significant amount of fines. Close control of distribution can be maintained to keep about 10 to 25 wt. % of the total catalyst in the reaction zone in the size range less than 32 microns. Accordingly, the fluidization regime is controlled to assure operation between the transition velocity and transport velocity.

Fluidized Bed Zeolite Reactor Operation

In addition to the aqueous methanol and olefinic components of the reactor feed, suitable oxygenate and or olefinic supplemental feedstreams may be added to the preferred MTG reactor unit. Non-deleterious components, such as lower paraffins and inert gases, may be present. The reaction severity conditions can be controlled to optimize yield of $C_3$-$C_5$ paraffins, olefinic gasoline or $C_6$-$C_8$ BTX hydrocarbons, according to product demand. It is understood that aromatic hydrocarbon and light paraffin production is promoted by those zeolite catalysts having a high concentration of Bronsted acid reaction sites. Accordingly, an important criterion is selecting and maintaining catalyst inventory to provide either fresh or regenerated catalyst having the desired properties. Reaction temperatures and contact time are also significant factors in the reaction severity, and the process parameters are followed to give a substantially steady state condition wherein the reaction severity is maintained within the limits which yield a desired weight ratio of propane to propene in the reaction effluent.

In a turbulent fluidized catalyst bed the conversion reactions are conducted in a vertical reactor column by passing hot reactant vapor or lift gas upwardly through the reaction zone at a velocity greater than dense bed transition velocity and less than transport velocity for the average catalyst particle. A continuous process is operated by withdrawing a portion of coked catalyst from the reaction zone, oxidatively regenerating the withdrawn catalyst and returning regenerated catalyst to the reaction zone at a rate to control catalyst activity and reaction severity to effect feedstock conversion.

Upgrading of olefins by hydrogen contributors in co-conversion reactors is taught by Owen et al in U.S. Pat. Nos. 4,788,365 and 4,090,949, and in application Ser. No. 179,726, filed 11 Apr. 1988, incorporated herein by reference. In a typical process, the methanol and olefinic feedstreams are converted in a catalytic reactor under elevated temperature conditions and moderate pressure (i.e. −100 to 2500 kPa) to produce a predominantly liquid product consisting essentially of $C_6^+$ hydrocarbons rich in gasoline-range paraffins and aromatics. The reaction temperature can be carefully controlled in the usual operating range of about 250° C. to 650° C., preferably at average reactor temperature of 350° C. to 500° C.

TRANSHYDROGENATION PROCESS OPERATION

An important unit operation in the conversion of iso-paraffins to their corresponding iso-olefins is a form of catalytic dehydrogenation known as transhydrogenation. This can be achieved by high temperature reaction using hydrogenation-dehydrogenation catalyst; however, it is within the inventive concept to employ other types of processes for transhydrogenation in this process step to effect removal of hydrogen from the $C_3$-$C_5$ intermediate alkanes. Various processes are known for producing isoalkene-rich by dehydrogenation. Typical processes are operated at elevated temperature (about 400°-650° C.) and moderate pressure using a metal oxide such as Cr oxide on a matrix such as alumina or silica. Other dehydrogenation techniques are disclosed in U.S. Pat. No. 4,546,204 (Parris).

EXAMPLE

A typical C4 refinery stream is converted to ether and gasoline by the present invention under continuous processing conditions. The feedstock consists essentially of 100 parts by weight of isobutene, 157.7 parts n-butene, and 66.9 parts isobutane. The C4 stream is contacted with 99.2 parts by weight of methanol and Amberlyst 15 catalyst under etherification conditions, and 264.2 parts of MTBE product is recovered from etherification effluent by distillation. Volatile unreacted methanol and C4− components are further converted over H-ZSM-5 catalyst in a fluidized bed reactor at about 330° C., 450 kPa and WHSV of 0.4. Butenes are recovered from zeolite conversion for recycle to the ether unit, and a product stream containing 144.1 parts $C_5+$ gasoline is recovered along with water and light gas byproduct streams. C4 paraffins rich in isobutane are recovered from the zeolite reactor effluent and transhydrogenated with 53.8 parts ethene contained in a C2 refinery stream. Total C3− light gas (about 66.6 parts) is recovered from the reactor system and the isobutene-rich transhydrogenation olefin product is sent to the etherification unit for conversion to MTBE.

Various modifications can be made to the system, especially in the choice of equipment and non-critical processing steps. While the invention has been described by specific examples, there is no intent to limit the inventive concept as set forth in the following claims.

We claim:

1. A process for conversion of olefinic light hydrocarbons to ether-rich liquid fuels and olefinic gasoline comprising;
    (a) reacting a fresh hydrocarbon stream containing $C_4+$ iso-alkene with lower aliphatic alcohol in an etherification zone in contact with an acidic etherification catalyst under etherification conditions whereby an effluent stream containing $C_5+$ tertiary-alkyl ether is produced;
    (b) separating said etherification effluent stream to provide a first liquid stream comprising $C_5+$ ether and a second stream comprising unreacted alcohol and $C_4+$ hydrocarbons;
    (c) contacting said second stream with acidic metallosilicate catalyst for conversion of oxygenates and olefins under olefin oligomerization and isomerization conditions at elevated temperature;
    (d) separating conversion effluent from step (c) to recover an intermediate hydrocarbon stream rich in $C_4+$ paraffinic hydrocarbon, a light gas stream, and a liquid product stream comprising $C_6+$ olefinic gasoline;
    (e) contacting said $C_4+$ intermediate hydrocarbon stream with lower alkene in the presence of transhydrogenation catalyst under transhydrogenation conditions whereby $C_{4+}$ paraffin is converted to $C_{4+}$ olefin, including iso-alkene;

(f) separating step (e) transhydrogenation effluent to recover $C_{4+}$ olefin containing iso-alkene; and (g) passing at least a portion of iso-alkene from step (f) to said etherification zone for co-conversion with said fresh hydrocarbon stream and alcohol to produce tertiary-alkyl ether.

2. The process of claim 1 wherein $C_{3-}$ olefins are recovered from step (f) and recycled to step (c).

3. The process of claim 1 wherein said step (b) second stream comprises an azeotropic mixture of methanol and olefinic hydrocarbons and said first stream comprises $C_{5+}$ ether-rich gasoline.

4. The process of claim 1 wherein the etherification conditions comprise a stoichiometric excess of said alcohol over $C_{4+}$ iso-alkenes whereby the etherification reaction equilibrium is shifted substantially toward the formation of $C_{5+}$ ethers.

5. The process of claim 4 wherein stoichiometric excess of methanol is about 1 to 33 percent.

6. The process of claim 1 wherein said metallosilicate catalyst comprises a shape-selective, medium pore, acid aluminosilicate zeolite-type catalyst.

7. The process of claim 1 wherein step (b) first stream comprises $C_{5+}$ ether-rich gasoline having high motor octane and research octane values.

8. An integrated continuous process for producing lower alkyl ethers and gasoline range hydrocarbons comprising the steps of:

(a) contacting a first liquid reaction mixture with an acid etherification catalyst in an etherification zone under etherification conditions, said first reaction mixture comprising $C_4$-$C_9$ hydrocarbons containing $C_4$-$C_7$ isoalkene components and $C_{5+}$ gasoline range non-etherifiable aliphatic components, and a lower aliphatic alcohol reactant;

(b) recovering an etherification reaction effluent containing $C_{5+}$ tertiary alkyl ether, gasoline range hydrocarbons, unreacted alcohol and light olefinic hydrocarbons;

(c) distilling the etherification reaction effluent to provide a first product stream comprising a liquid mixture of $C_{5+}$ ether and gasoline range hydrocarbons, and a second volatile low molecular weight reaction mixture comprising unreacted alcohol and light aliphatic hydrocarbons; and (d) contacting the second reaction mixture with an acid medium pore metallosilicate zeolite catalyst at elevated temperature to convert the alcohol and light olefinic hydrocarbons to a second effluent stream having average molecular weight greater than the second reaction mixture and containing $C_{4+}$ branched aliphatic hydrocarbon and $C_{5+}$ hydrocarbon;

(e) separating the second effluent stream to obtain a second $C_{5+}$ hydrocarbon liquid product and a $C_{4-}$ aliphatic hydrocarbon stream;

(f) contacting the $C_{4-}$ aliphatic hydrocarbon stream with ethene in a transhydrogenation zone under catalytic reaction conditions to produce isobutene;

(g) passing step (f) C4 transhydrogenation product comprising isobutene to step (a) etherification zone for etherification and conversion to high octane gasoline.

9. The process of claim 8 wherein the first reaction mixture consists essentially of a mixture of butene isomers, light olefinic naphtha and methanol, said methanol being present in at least 1% excess of the isoalkene components; wherein the second reaction mixture comprises unreacted methanol, paraffins and butylenes; and wherein the zeolite catalyst comprises aluminosilicate having the structure of ZSM-5.

10. The process of claim 9 wherein the second reaction mixture is supplemented with added light olefin.

11. The process of claim 9 wherein the first product stream comprises MTBE, TAME and unreacted naphtha.

12. A continuous process for converting olefinic hydrocarbon and alcohol to alkyl tert-alkyl ethers and gasoline comprising the steps of:

contacting lower alkanol feedstock with a $C_{4+}$ hydrocarbon feedstream rich in isobutene in a first etherification catalytic reaction zone for contact with acid etherification catalyst under etherification process conditions for converting alkanol and isobutene to predominantly alkyl tertiary-butyl ether;

fractionating etherification effluent to recover overhead vapor containing unreacted alkanol and light olefinic hydrocarbon and to recover liquid product containing alkyl tertiary-butyl ether;

catalytically converting said overhead vapor in contact with medium pore acid zeolite catalyst in a second catalytic reaction zone to provide predominantly liquid $C_{5+}$ hydrocarbon product along with $C_3$-$C_4$ aliphatic hydrocarbon intermediate product rich in isobutane, and a light gas by-product;

separating the light gas, $C_3$-$C_4$ isobutane-rich intermediate and $C_{5+}$ hydrocarbon product;

transhydrogenating isobutane-rich intermediate by reaction with ethene or propene to produce isobutene; and recycling isobutene from transhydrogenation effluent for reaction with alkanol feedstock.

13. The process of claim 12 wherein the acid etherification catalyst comprises ion exchange resin, wherein the alkanol feedstock consists essentially of methanol.

14. The process of claim 12 wherein the intermediate includes about 5 to 30% isobutane, based on total hydrocarbon effluent from the second reaction zone.

15. In the process for the production of methyl tertiary alkyl ethers comprising reacting a mixture comprising methanol and $C_{4+}$ iso-olefins-rich hydrocarbons in contact with acid etherification catalyst under etherification conditions in an etherification zone to produce a product stream comprising $C_{5+}$ methyl tertiary alkyl ethers, unreacted methanol and hydrocarbons; separating said product stream by aqueous extraction and distillation of unreacted methanol, recycling unreacted methanol and recovering a hydrocarbon stream rich in $C_{5+}$ methyl tertiary alkyl ethers, the improvement comprising;

separating said product stream by distillation to produce an overhead vapor stream comprising unreacted methanol and $C_{4+}$ hydrocarbons, and a bottom liquid stream comprising hydrocarbons rich in $C_{5+}$ ethers; recovering and recycling the major portion of said unreacted methanol;

passing said overhead stream to an oxygenates and olefins conversion zone in contact with medium pore shape selective metallosilicate catalyst particles under conversion condition whereby oxygenates and/or olefins are converted to conversion products having higher average molecular weight;

recovering said conversion products and passing the portion thereof comprising $C_4$–$C_5$ aliphatic hydrocarbons to a transhydrogenation zone for reaction with lower olefin under transhydrogenation conditions whereby $C_4$–$C_5$ olefins are produced;

recovering said $C_4$–$C_5$ olefins and passing said olefins to said etherification zone in conjunction with fresh methanol and $C_4+$ iso-olefins-rich hydrocarbons.

16. The process of claim 15 wherein etherification reaction mixture comprise a stoichiometric excess of methanol whereby the yield of methyl tertiary alkyl ethers is increased.

17. The process of claim 16 wherein the methyl tertiary alkyl ethers comprise methyl tertiary butyl ether and methyl tertiary-amyl ether.

18. In the process for etherifying iso-alkene by partial reaction with alkanol to produce tertiary alkyl ether wherein isoparaffin is dehydrogenated to provide at least a portion of iso-alkene etherification reactant; the improvement which comprises:

upgrading volatile etherification reaction components including unreacted alkanol and alkene by contacting said volatile reaction components with shape selective medium pore acid zeolite catalyst at elevated temperature to provide $C_5+$ liquid hydrocarbon product and a paraffinic intermediate rich in isobutane;

contacting at least a portion of said paraffinic intermediate containing isobutane with a lower alkene under transhydrogenation conditions to convert isobutane to isobutene; and further etherifying the isobutene by reaction with alkanol.

19. In the process for etherifying iso-alkene by partial reaction with alkanol to produce tertiary alkyl ether wherein isoparaffin is dehydrogenated to provide at least a portion of iso-alkene etherification reactant; the improvement which comprises:

upgrading volatile etherification reaction components including unreacted alkanol and alkene by contacting said volatile reaction components with shape selective medium pore acid zeolite catalyst at elevated temperature to provide $C_5+$ liquid hydrocarbon product and a paraffinic intermediate rich in isobutane;

contacting at least a portion of said paraffinic intermediate containing isobutane with a lower alkene under transhydrogenation conditions to convert isobutane to isobutene; and further etherifying the isobutene by reaction with alkanol.

* * * * *